United States Patent [19]

Morimoto

[11] Patent Number: 5,262,563
[45] Date of Patent: Nov. 16, 1993

[54] PROCESS FOR PRODUCING SULFOALKYL-SUBSTITUTED HYDROXYLAMINES

[75] Inventor: Kiyoshi Morimoto, Minami-Ashigara, Japan

[73] Assignee: Fuji Photo Film Co., Ltd., Minami-Ashigara, Japan

[21] Appl. No.: 551,087

[22] Filed: Jul. 11, 1990

[30] Foreign Application Priority Data

Jul. 25, 1989 [JP] Japan ................... 1-191964

[51] Int. Cl.$^5$ ................. C07C 239/00; C07C 143/06; C07C 143/14
[52] U.S. Cl. ................... 562/104; 562/102; 562/105; 562/106; 562/107; 564/301
[58] Field of Search .............. 562/104, 107, 102, 115

[56] References Cited

U.S. PATENT DOCUMENTS

| | | | |
|---|---|---|---|
| 2,658,072 | 5/1951 | Kosmin et al. | 562/104 |
| 2,693,488 | 11/1954 | Sexton et al. | 562/104 |
| 3,388,154 | 6/1968 | Bitar et al. | 562/104 |
| 3,664,278 | 2/1972 | Klemchuk | 260/45.8 N |
| 3,778,464 | 12/1973 | Klemchuk | 562/107 |
| 4,582,651 | 4/1986 | Ishii et al. | 562/102 |

FOREIGN PATENT DOCUMENTS

| | | | |
|---|---|---|---|
| 0277273 | 3/1990 | Fed. Rep. of Germany | 562/104 |
| 0059959 | 4/1983 | Japan | 562/104 |
| 1263199 | 2/1972 | United Kingdom | 560/171 |
| 1264920 | 2/1972 | United Kingdom | 560/171 |

*Primary Examiner*—José G. Dees
*Assistant Examiner*—Keith MacMillan
*Attorney, Agent, or Firm*—Burns, Doane, Swecker & Mathis

[57] ABSTRACT

There is provided a process for producing sulfoalkyl-substituted hydroxylamines useful as preservatives to be added to a color developer for photosensitive materials. In this process, the sulfoalkyl-substituted hydroxylamines can be easily synthesized by reacting a specified alkylating agent, cyclic sulfonic ester, vinylsulfonic acid or sulfoalkyl-substituted acrylamide with a hydroxylamine.

18 Claims, No Drawings

PROCESS FOR PRODUCING SULFOALKYL-SUBSTITUTED HYDROXYLAMINES

BACKGROUND OF THE INVENTION

The present invention relates to a process for producing sulfoalkyl-substituted hydroxylamines useful as an additive for a photographic processing solution.

Although sulfoalkyl-substituted hydroxylamines are useful as a preservative to be added to a color developer for photosensitive materials such as photographic sensitive materials, no process for their production is disclosed in the literature. It is thus desirable to develop a new technique of producing them on an industrial scale. In particular, the development of a process for easily synthesizing the sulfoalkyl-substituted hydroxylamines from readily available starting materials is eagerly desired.

The following three processes are possible for synthesizing hydroxylamines: (1) a process wherein an amine compound is oxidized, (2) a process wherein an N-oxide of a tertiary amine is thermally decomposed (diethylhydroxylamine is synthesized on a large scale by this process) and (3) a process wherein an unsubstituted hydroxylamine or monosubstituted hydroxylamine is alkylated to form a monosubstituted or disubstituted hydroxylamine.

SUMMARY OF THE INVENTION

Through an investigation into the production of sulfoalkyl-substituted hydroxylamines by these processes, the inventor found that, unexpectedly, side reactions are relatively slight in the process (3) and this process is suitable for the mass production. In particular, the inventor found that sulfoalkyl-substituted hydroxylamines can be easily synthesized by reacting an alkylating agent, cyclic sulfonic ester, vinylsulfonic acid or sulfoalkyl-substituted acrylamide, all of which are readily available on the market, with a hydroxylamine. The present invention has been completed on the basis of this finding.

The present invention provides a process for producing a sulfoalkyl-substituted hydroxylamine of the general formula [I]:

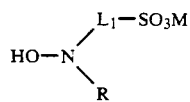  [I]

wherein $L_1$ represents a divalent organic group, R represents a hydrogen, alkyl group or group of the formula: $-L_1-SO_3M$, M being a cation, which comprises reacting a hydroxylamine of the general formula [II]:

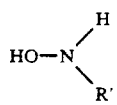  [II]

wherein R' represents a hydrogen or an alkyl group with one of the compounds of the following general formulae [III] to [VI]:

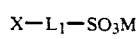  [III]

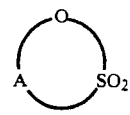  [IV]

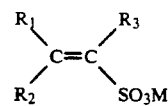  [V]

and

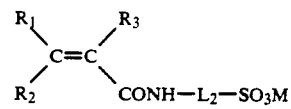  [VI]

wherein A represents an alkylene group, $R_1$ to $R_3$ each represent a hydrogen atom or alkyl group, X represents a halogen atom, alkylsulfonyloxy group or arylsulfonyloxy group and $L_2$ represents a divalent organic group.

DESCRIPTION OF THE PREFERRED EMBODIMENTS $L_1$ in the above formula is preferably a divalent organic group comprising an unsubstituted or substituted alkylene group, —CO— or —NH— singly or a combination thereof. M is preferably a hydrogen atom, alkali metal or ammonium salt. The alkyl group of R, R' and $R_1$ to $R_3$ may be either straight chain or branched and either unsubstituted or substituted. The alkyl group has preferably 1 to 10 carbon atoms. $R_1$ to $R_3$ may be the same or different from one another. A may have a substituent.

A detailed description will be made on the compounds of the general formulae [I] to [VI] in the present invention.

$L_1$ and $L_2$ each represent a divalent organic group comprising a substituted or unsubstituted alkylene group, —CO— or —NH— singly or a combination thereof. The alkylene group is a substituted or unsubstituted, straight chain or branched alkylene group having 1 to 10 carbon atoms, preferably 1 to 5 carbon atoms. The substituents include hydroxyl group and carboxyl group. Preferred examples of $L_1$ and $L_2$ are alkylene groups and divalent organic groups comprising a combination of an alkylene group and carbamoyl group. M represents a hydrogen atom, alkali metal (lithium, sodium or potassium) or ammonium salt. R represents a hydrogen atom or substituted or unsubstituted alkyl group. The substituents include sulfo group, hydroxyl group, carboxyl group and carbamoyl group which may be substituted with a sulfoalkyl group. R is preferably a hydrogen atom, unsubstituted alkyl group, sulfo group or alkyl group substituted with a carbamoyl group which may be substituted with a sulfoalkyl group. X represents a halogen atom (fluorine atom, chlorine atom or bromine atom), alkylsulfonyloxy group (such as methanesulfonyloxy group) or arylsulfonyloxy group (such as benzenesulfonyloxy group or p-toluenesulfonyloxy group). X is preferably a halogen atom (chlorine atom or bromine atom). A represents a substituted or unsubstituted alkylene group having 3 to 10 carbon atoms. The substituents include alkyl groups. $R_1$, $R_2$ and $R_3$ may be the same or different from one another and each represents a hydrogen atom or substituted or unsubstituted alkyl group. A preferred example of $R_1$, $R_2$ and $R_3$ is hydrogen atom.

Examples of the sulfoalkyl-substituted hydroxylamines of the general formula [I] which can be synthesized by the process of the present invention are given below, which by no means limit the present invention:

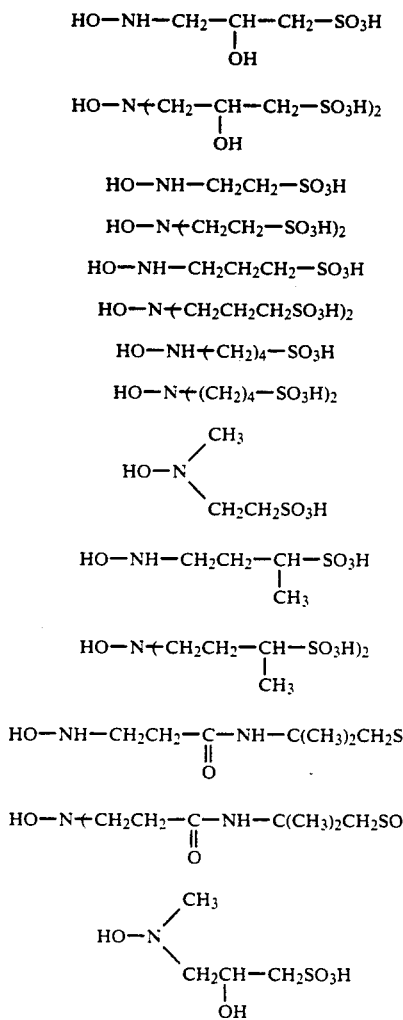

A detailed description will be made on the embodiments of the present invention:

Synthesis process (a) wherein a compound of the general formula [III] is used This process comprises a substitution reaction of a hydroxylamine with an alkylating agent (a sulfo-substituted alkyl halide or sulfo-substituted alkyl ester of sulfonic acid). When the starting hydroxylamine is in the form of its hydroxide or sulfate, it is preferably neutralized with a suitable base (such as sodium hydroxide, sodium carbonate or sodium hydrogencarbonate). The neutralization is preferred in all the processes which will be described below. The halogen atom of the sulfo-substituted alkyl halide is preferably chlorine atom or bromine atom. The sulfonic acid is preferably methanesulfonic acid, benzenesulfonic acid or p-toluenesulfonic acid. Since an acid is formed as the substitution reaction proceeds, a base can be added in the amount needed for neutralizing the acid. The bases usable herein include sodium hydroxide, potassium hydroxide, lithium hydroxide, sodium carbonate, potassium carbonate, sodium hydrdogencarbonate, potassium hydrogencarbonate, triethylamine and pyridine.

The reaction must be controlled, since the hydroxylamine has a high reactivity and relatively easily forms a disubstituted or trisubstituted product. In the synthesis of a monosubstituted hydroxylamine by the substitution reaction of an unsubstituted hydroxylamine, the production of a disubstituted product must be inhibited. The amount of the unsubstituted hydroxylamine used is preferably 1 to 5 mol, more preferably 2 to 5 mol, per mol of the alkylating agent. In the synthesis of a disubstituted hydroxylamine by the substitution reaction of an unsubstituted hydroxylamine, the production of a trisubstituted product (to form a corresponding compound having three alkyl groups bonded with N) must be inhibited. The trisubstituted product is often highly crystalline and its isolation or purification is often difficult. It is effective to suitably adjust the amount of the reagent. The amount of the alkylating agent used is preferably in the range of 1 to 2.5 mol, more preferably 1.2 to 2.2 mol, per mol of the starting material.

The reaction solvent must be such that the starting material is soluble therein. It is preferably a mixture of water with another solvent or water alone.

The reaction temperature ranges from 0° C. to 100° C. It is preferably as low as possible within the range of temperatures at which the reaction proceeds. The procedure of the reaction can be known from NMR or the like.

The product can be isolated in the form of an alkali metal (sodium or potassium) salt of sulfonic acid or as betaine. If necessary, an ion exchange resin is usable.

Synthesis process (b) wherein a compound of the general formula [IV] is used This process comprises a substitution reaction of a hydroxylamine with a cyclic sulfonic ester. The cyclic sulfonic ester is preferably 1,3-propanesultone or 1,4-butanesultone. Since a sulfonic acid is formed as the substitution reaction proceeds, a base can be added in the amount needed for neutralizing the acid. The bases usable for this purpose are the same as those usable in the above-described process (a).

The cyclic sulfonic ester having a high activity tends to form by-products. In the synthesis of a monosubstituted hydroxylamine by the substitution reaction of an unsubstituted hydroxylamine, the production of a disubstituted product must be inhibited. The amount of the unsubstituted hydroxylamine used is preferably 1 to 10 mol, more preferably 3 to 10 mol, per mol of the alkylating agent. When 1,3-propanesultone is used as the starting material, it is preferably used in an amount of at least 5 mol per mol of the alkylating agent. In the synthesis of a disubstituted hydroxylamine by the substitution reaction of an unsubstituted hydroxylamine, the production of a trisubstituted product (a corresponding compound having three alkyl groups bonded with N) must be inhibited. The trisubstituted product is often highly crystalline and its isolation or purification is often difficult. It is effective to suitably adjust the amount of the reagent. The amount of the alkylating agent used is preferably in the range of 1 to 2.5 mol, more preferably 1.2 to 2.0 mol. Since the sulfonic ester has a high reactivity, it is important to inhibit side reactions.

The reaction solvent, reaction temperature and isolation method are the same as those described in process (a).

Synthesis process (c) wherein a compound of the general formula [V] is used

This process comprises an addition reaction of a hydroxylamine with a vinylsulfonate. A preferred example of the vinylsulfonic acids is unsubstituted vinylsulfonic acid.

In the synthesis of a monosubstituted hydroxylamine by a substitution reaction of an unsubstituted hydroxylamine, the production of a disubstituted product must be inhibited. The amount of the unsubstituted hydroxylamine used is preferably 1 to 10 mol, more preferably 3 to 10 mol, per mol of the vinylsulfonic acid. In the synthesis of a disubstituted hydroxylamine by the addition reaction of an unsubstituted hydroxylamine, the amount of the vinylsulfonic acid is preferably 1 to 2.5 mol, more preferably 1.2 to 2.0 mol, per mol of the starting hydroxylamine. This process is superior to the processes (a) and (b) in that the side reaction to form a trisubstituted product occurs only slightly and the yield of the intended product is high.

The reaction solvent, reaction temperature and isolation method are the same as those described in process (a).

Synthesis process (d) wherein a compound of the general formula [VI] is used

This process comprises an addition reaction of a hydroxylamine with a sulfoalkyl-substituted acrylamide.

In the synthesis of a monosubstituted hydroxylamine by a substitution reaction of an unsubstituted hydroxylamine, the production of a disubstituted product must be inhibited. The amount of the unsubstituted hydroxylamine used is preferably 1 to 10 mol, more preferably 3 to 10 mol, per mol of the sulfoalkyl-substituted acrylamide. In the synthesis of a disubstituted hydroxylamine by the addition reaction of an unsubstituted hydroxylamine, the amount of the sulfoalkyl-substituted acrylamide is preferably 1 to 2.5 mol, more preferably 1.2 to 2.0 mol, per mol of the starting hydroxylamine. This process is also superior to the processes (a) and (b) in that the side reaction forming a trisubstituted product occurs only slightly and the yield of the intended product is high.

The reaction solvent, reaction temperature and isolation method are the same as those described in process (a).

It is apparent that the alkylation reaction processes (c) and (d) are excellent, since side reactions occur only slightly and the yield of the intended product is high.

According to the process of the present invention, sulfoalkyl-substituted hydroxylamines can be easily synthesized from starting materials readily available on the market. Thus the production of the compounds useful as a material for a photographic processing solution, etc. on an industrial scale is made possible. The utility value thereof is high.

The following Examples will further illustrate the present invention.

EXAMPLE 1

Synthesis by process (a)

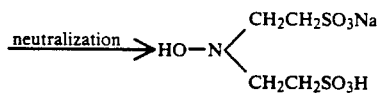

monosodium salt of compound (4)

11.5 g of sodium hydroxide and 96 g of sodium chloroethanesulfonate were added to 200 ml of an aqueous solution of 20 g of hydroxylamine hydrochloride. 40 ml of an aqueous solution of 23 g of sodium hydroxide was slowly added thereto over 1 h while the temperature was kept at 60° C. After keeping the temperature at 60° C. for an additional 3 h, the reaction liquid was concentrated under reduced pressure, 200 ml of concentrated hydrochloric acid was added thereto and the mixture was heated to 50° C. The insoluble matter was taken out by filtration. 500 ml of methanol was added to the filtrate to obtain 41 g (yield: 53%) of sodium salt of the intended product [compound (4)] in the form of crystals.

$^1$N NMR spectrum (D$_2$O) δ 3.8 to 4.0 (4H, br), 3.4 (4H, t, J=7.0).

EXAMPLE 2

Synthesis by process (a)

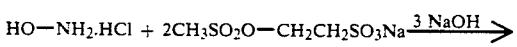

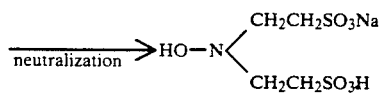

monosodium salt of compound (4)

11.5 g of sodim hydroxide and 130 g of sulfoethyl methanesulfonate were added to 250 ml of an aqueous solution of 20 g of hydroxylamine hydrochloride. 40 ml of an aqueous solution of 23 g of sodium hydroxide was slowly added thereto over 1 h while the temperature was kept at 40° C. After keeping the temperature at 40° C. for an additional 5 h, the reaction liquid was concentrated under reduced pressure, 200 ml of concentrated hydrochloric acid was added thereto and the mixture was heated to 50° C. The insoluble matter was taken out by filtration. 500 ml of methanol was added to the filtrate to obtain 33 g (yield: 42%) of monosodium salt of the intended product [compound (4)] in the form of crystals.

$^1$H NMR spectrum (D$_2$O) δ 3.8 to 4.0 (4H, br), 3.4 (4H, t, J=7.0).

EXAMPLE 3

Synthesis by process (a)

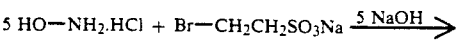

-continued

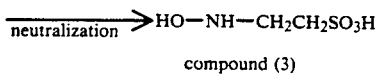

compound (3)

47.4 g of sodium hydroxide was added to 300 ml of an aqueous solution of 82.4 g of hydroxylamine hydrochloride. 50 g of sodium bromoethanesulfonate was slowly added thereto over 1 h while the temperature was kept at 20° C. After keeping the temperature at 20° C. for an additional 10 h, the reaction liquid was concentrated under reduced pressure, 100 ml of concentrated hydrochloric acid was added thereto and the mixture was heated to 50° C. The insoluble matter was removed by filtration. 300 ml of methanol and 300 ml of isopropyl alcohol were added to the filtrate to obtain 8.4 g (yield: 25%) of the intended product [compound (3)] in the form of crystals.

$^1$H NMR spectrum (D$_2$O) δ 3.75 (4H, t, J=7.0), 3.4 (4H, t, J=7.0).

EXAMPLE 4

Synthesis by process (a)

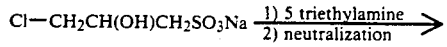

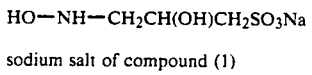

sodium salt of compound (1)

52 g of triethylamine was added to 300 ml of an aqueous solution of 35.4 g of hydroxylamine hydrochloride. 20 g of sodium 2-chloro-3-hydroxypropanesulfonate was slowly added thereto over 1 h while the temperature was kept at 20° C. After keeping the temperature at 40° C. for an additional 10 h, the reaction liquid was concentrated under reduced pressure. 100 ml of concentrated hydrochloric acid was added thereto and the mixture was heated to 50° C. The insoluble matter was taken out by filtration and the filtrate was concentrated under reduced pressure until the volume thereof was reduced to a half. Then sodium hydroxide was added thereto to adjust pH thereof to 7. 200 ml of methanol and 200 ml of isopropyl alcohol were added thereto to obtain 5.4 g (yield: 31%) of sodium salt of the intended product [compound (1)] in the form of crystals.

$^1$H NMR spectrum (D$_2$O) δ 4.35 (1H), 3.1 (2H), 2.8 (2H).

EXAMPLE 5

Synthesis by process (b)

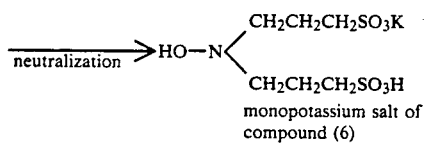

monopotassium salt of compound (6)

65.5 g of potassium carbonate was added to 200 ml of an aqueous solution of 30 g of hydroxylamine hydrochloride. 63.2 g of 1,3-propanesultone was slowly added thereto over 1 h while the temperature was kept at 5° C. The reaction liquid was concentrated under reduced pressure. 100 ml of concentrated hydrochloric acid was added thereto and the mixture was heated to 50° C. The insoluble matter was removed by filtration. 300 ml of methanol was added to the filtrate to obtain 21 g (yield: 26%) of monopotassium salt of the intended product [compound (6)] in the form of crystals.

$^1$H NMR spectrum (D$_2$O) δ 3.8 (4H, t, J=7.0), 3.0 (4H, t, J=7.0), 2.2 (4H).

EXAMPLE 6

Synthesis by process (c):

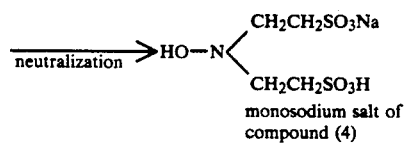

monosodium salt of compound (4)

10 g of hydroxylamine hydrochloride and 5.8 g of sodium hydroxide were added to 142 g of 25% aqueous solution of sodium vinylsulfonate. They were heated under reflux for 3 h. The reaction liquid was concentrated under reduced pressure. 100 ml of concentrated hydrochloric acid was added thereto and the mixture was heated to 50° C. The insoluble matter was taken out by filtration. 200 ml of methanol and 100 ml of isopropyl alcohol were added to the filtrate to obtain 25.9 g (yield: 70%) of monosodium salt of the intended product [compound (4)] in the form of crystals.

$^1$H NMR spectrum (D$_2$O) δ 3.8 to 4.0 (4H, br), 3.4 (4H, t, J=7.0).

EXAMPLE 7

Synthesis by process (d)

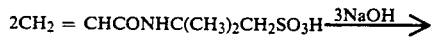

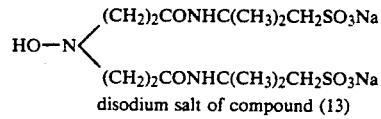

disodium salt of compound (13)

6.5 g of sodium hydroxide and 20.7 g of the above-mentioned alkyl-substituted acrylamide were added to 40 ml of an aqueous solution of 3.5 g of hydroxylamine hydrochloride. They were heated under reflux for 1 h. The reaction liquid was concentrated under reduced pressure. 200 ml of methanol was added thereto and insoluble common salt was removed. The filtrate was concentrated and ethanol was added thereto to obtain dihydrate of disodium salt of the intended product [compound (13)] in the form of crystals.

17.6 g (yield: 67%)

$^1$H NMR spectrum (D$_2$O) δ 3.4 (4H, S), 2.95 (4H, t, J=7.0), 2.45 (4H, t, J=7.0), 1.45 (12H, S).

EXAMPLE 8

Synthesis by process (c)

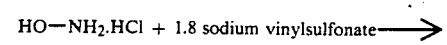

-continued

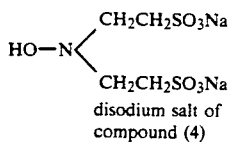
disodium salt of compound (4)

468 g of 25% aqueous solution of sodium vinylsulfonate was added to 33 g of 50% aqueous solution of hydroxylamine hydrochloride. They were heated under reflux for 2 h. 2500 ml of methanol was added to the resultant to obtain 96.0 g (yield: 73%) of disodium salt of the intended product [compound (4)] in the form of crystals.

$^1$H NMR spectrum (D$_2$O) δ 3.0 to 3.4 (8H, br)

What is claimed is:

1. A process for producing a sulfoalkyl-substituted hydroxylamine of the general formula (I):

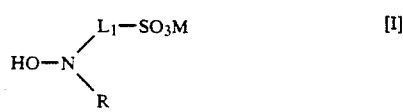

wherein L$_1$ represents an alkylene group, R represents a hydrogen, alkyl group or group of the formula:
—L$_1$—SO$_3$M, M being a cation,
which comprises reacting a hydroxylamine of the general formula (II)

wherein R' represents a hydrogen or an alkyl group with one of the compounds of the following formulae (V):

wherein R$_1$ to R$_3$ each represent a hydrogen atom or alkyl group.

2. A method of claim 1 wherein the alkylene group has 1 to 10 carbon atoms.

3. A method of claim 1 wherein the alkyl group in formulae (I), (II) and (V) has 1 to 10 carbon atoms.

4. A method of claim 1 wherein an amount of a compound to the general formula (II) wherein R' is a hydrogen is 1 to 10 mol, per mol of a compound of formula (V) to prepare a compound of the formula (I) wherein R is a hydrogen.

5. A method of claim 1 wherein an amount of a compound of formula (V) is 1 to 2.5 mol, per mol of a compound of the general formula (II) wherein R' is a hydrogen to prepare a compound of the formula (I) wherein R is L$_1$—SO$_3$M.

6. A method of claim 1 wherein there is used a reaction solvent in which compounds of formulae (II) and (V) are soluble therein.

7. A method of claim 1 wherein the reaction is carried out at a temperature of 0° to 100° C.

8. The method of claim 5 wherein there is used a reaction solvent in which compounds of formula (II) and (V) are soluble therein and the reaction is carried out a temperature of 0° to 100° C.

9. The method according to claim 6 wherein the reaction solvent includes water.

10. The method according to claim 8 wherein the reaction solvent includes water.

11. A method of claim 1 wherein R in formula (I) is a hydrogen or group of the formula:
—L$_1$—SO$_3$M, L$_1$ being an alkylene group and M being a cation, and R' in formula (II) is a hydrogen.

12. A method of claim 11 wherein the alkylene group has 1 to 10 carbon atoms.

13. A method of claim 11 wherein the alkyl group in formula (V) has 1 to 10 carbon atoms.

14. A method of claim 11 wherein an amount of a compound to the general formula (II) is 1 to 10 mol, per mol of a compound of formula (V) to prepare a compound of the formula (I) wherein R is a hydrogen.

15. A method of claim 11 wherein an amount of a compound of formula (V) is 1 to 2.5 mol per mol of a compound of the general formula (II) to prepare a compound of the formula (I) and further wherein R is L$_1$—SO$_3$M.

16. A method of claim 11 further comprising a reaction solvent in which compounds of formulae (II) and (V) are soluble therein.

17. The method according to claim 16 wherein the reaction solvent includes water.

18. A method of claim 11 wherein the reaction is carried out at a temperature of 0° to 100° C.

* * * * *